United States Patent [19]

Wätjen et al.

[11] Patent Number: 4,870,073
[45] Date of Patent: Sep. 26, 1989

[54] HETEROCYCLIC COMPOUNDS AND THEIR PREPARATION AND USE

[75] Inventors: Frank Wätjen; Mogens Engelstoft, both of Vaerloese, Denmark

[73] Assignee: A/S Ferrosan, Soborg, Denmark

[21] Appl. No.: 912,777

[22] Filed: Sep. 26, 1986

[30] Foreign Application Priority Data

Oct. 17, 1985 [DK] Denmark .................... 4768/85

[51] Int. Cl.$^4$ .................... C07D 487/04; A61K 31/55
[52] U.S. Cl. .................... 514/214; 540/579; 540/548; 540/562
[58] Field of Search .................... 540/579; 514/214

[56] References Cited

U.S. PATENT DOCUMENTS 4,774,245  9/1988  Wätjen .................... 514/250

*Primary Examiner*—Robert Gerstl
*Attorney, Agent, or Firm*—Gordon W. Hueschen

[57] ABSTRACT

New heterocyclic derivatives having the general formula:

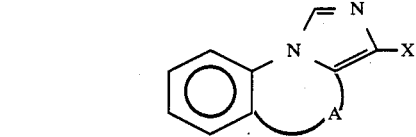

wherein
X is

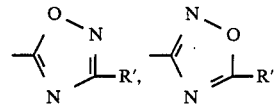

or $CO_2R'$ wherein
R' is $C_{1-6}$-alkyl, $C_{3-7}$-cycloalkyl, or $C_{1-3}$-alkoxymethyl, and
A— is —$(CH_2)_n$—Y—$(CH_2)_m$—,
wherein n and m are 0 or 1 and —Y— is —O—, —S—, —$CH_2$—, or —NR"—, wherein R" is hydrogen or $C_{1-6}$-alkyl.

The compounds are useful in psychopharmaceutical preparations as anticonvulsants, anxiolytics, hypnotics, and nootropics and in human and animal health as anthelmintics, etco- and endoparasiticides, insecticides and acaricides.

7 Claims, No Drawings

HETEROCYCLIC COMPOUNDS AND THEIR PREPARATION AND USE

The present invention relates to therapeutically active heterocyclic compounds, a method of preparing the same, pharmaceutical compositions comprising the compounds, and to methods of treating therewith. The novel compounds are useful in psychopharmaceutical applications, e.g., in the treatment of central system ailments, for example, as anticonvulsants or anxiolytics. The novel compounds of the invention are also useful as anthelmintics, ecto- and endoparasiticides insecticides and acaricides in human and animal health.

It is well known (M. Nielsen et al., Biochem. Pharmacol. Vol. 34, 3633-42 (1985)) that central nervous system (CNS) depressing agents such as etomidate, etazolate (SQ 20.009) and carbazolate affect the binding of t-butylbicyclo-phosphorothionate (TBPS) binding to the anion gating mechanism of the GABA/benzodiazepine receptor chloride channel complex.

Further it is well known that the anthelmintic activity of ivermectin is mediated through its binding to the chloride ion channel.

It has now been dound that the members of a novel group of heterocyclic compounds have strong affinity for the TBPS binding site, being able to displace radioactively labelled TBPS from such binding sites, which makes the novel compounds useful in psychopharmacetical preparations as anticonvulsants, anxiolytics, hypnotics, sedatives, nootropics, and as anthelmintics, ecto- and endoparasiticides, insecticides and acaricides in human and animal health.

Accordingly, it is an object of the invention to provide such novel heterocyclic compounds.

The novel compounds of the invention are heterocyclic compounds having the general formula I

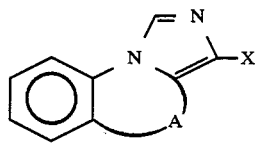

wherein
X is

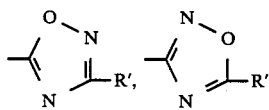

or $CO_2R'$
werein
R' is $C_{1-6}$-alkyl, $C_{3-7}$-cycloalkyl, or $C_{1-3}$-alkoxymethyl, and
—A— is —$(CH_2)_n$—Y—$(CH_2)_m$—,
wherein n and m are 0 or 1 and —Y— is —O—, —S—, —$CH_2$—, or —NR"—, wherein R" is hydrogen or $C_{1-6}$-alkyl.

The pharmacological properties of the compounds of the invention can be illustrated by determining their capability for displacing $^{35}(S)$-TBPS from the anion gating binding site.

The displacement activity of the compounds of the invention may be found by determining the $IC_{50}$ value.

The $IC_{50}$ value represents the concentration (ng/ml) which causes displacement of 50% of the specific binding of $^{35}(S)$TBPS. Cerebral cortex (0.1-1 g) from male Wistar rats (200–300 g) is homogenized for 5-10 seconds with an Ultra-Turrax ™ homogenizer in 10 ml of Tris-citrate (50 mM), pH 7.1. The homogenizer is rinsed with 10 ml of buffer and the combined suspension centrifuged for 10 min at 27,000×g. The pellet is homogenized as before in 2×10 ml of buffer and centrifuged min at 27,000×g. The pellet is frozen overnight (at −70° C.), thawed and washed twice. In each wash step the pellet is homogenized in 2×10 ml of 50 mM Tris-citrate and centrifuged at 27,000×g for 10 min. The pellet is again frozen overnight (at −70° C.), thawed and washed twice. In each wash step the pellet is again homogenized in 2×10 ml of 50 mM Tris-citrate and centrifuged at 27,000×g for 10 min. The final pellet is homogenized in Tris-citrate (50 mM), NaCl (1M) (100 ml per g of original tissue) and used for binding assays.

To an aliquot of 0.5 ml of tissue suspension is added 25 1 of test solution and 25 µl of $^{35}S$-TBPS (1 nM, final concentration), mixed and incubated for 60 min at 25° C. Non-specific binding is determined in duplicate using picrotoxinin (10 µg/ml, final concentration) as the test substance. After incubation, samples are added to 10 ml of ice-cold buffer (Tris-citrate (50 mM), NaCl (1M)) and poured directly onto Whatman GF/C glass fiber filters under suction and immediately washed again with 10 ml of ice-cold buffer. The amounts of radioactivity on the filters are determined by conventional liquid scintillation counting. Specific binding is total binding minus non-specific binding.

Test substances are dissolved in 10 ml water (if necessary, acidified by 25 µl 1N HCl and heated on a steambath for less than 5 minutes) at a concentration of 0.22 mg/ml. Dilutions are made in water.

Concentrations of 10, 100, 1000 ng/ml (final concentration) are added to duplicate assays. 25-75% inhibition of specific binding must be obtained before calculation of $IC_{50}$.

The test value will be given as $IC_{50}$ (the concentration (ng/ml) of the test substance which inhibits the specific binding of $^3H$-flunitrazepam by 50%).

$$IC_{50} = \text{(Applied test substance concentration)} \times \frac{1}{\left(\frac{C_o}{C_x} - 1\right)} \text{ ng/ml}$$

where $C_o$ is specific binding in control assays and $C_x$ is the specific binding in the test assay.

Test results obtained by testing some compounds of the present invention will appear from the following table 1.

TABLE 1

| -A- | X | in vitro ng/ml |
|---|---|---|
| $-CH_2-S-CH_2$ | 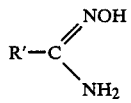 | 350 |
| $-CH_2CH_2CH_2-$ | 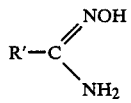 | 360 |
| $-CH_2CH_2CH_2$ | 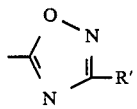 | 110 |
| $-CH_2CH_2CH_2-$ | 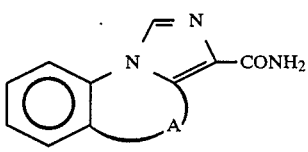 | 590 |
| $-CH_2CH_2CH_2-$ | $-CO_2C_2H_5$ | 350 |
| Etazolate | | 3500 |

The invention also relates to a method of preparing the above mentioned compounds. This method comprises (a) reacting a compound having the general formula II

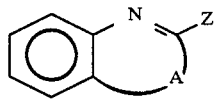  (II)

wherein —A— has the meaning defined above and Z is a leaving group, with a compound having the general formula $$CN-CH_2-X$$

under basic conditions to form a compound of the general formula I wherein X and —A— have the meanings set forth above, (b) reacting a reactive derivative of a compound having the general formula III

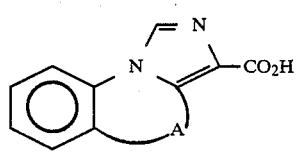  (III)

wherein —A— has the meaning defined above, with a compound having the general formula IV

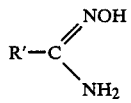  (IV)

wherein R' has the meaning defined above to form a compound of the general formula I wherein —A— has the meaning set forth above and wherein X is

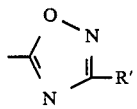

wherein R' has the meaning defined above, (c) reacting a compound having the general formula V

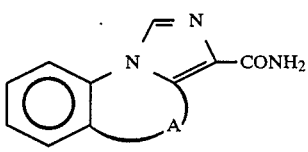  (V)

wherein —A— has the meaning set forth above, with a compound having the general formula VI $$R'-C(OCH_3)_2N(CH_3)_2 \quad (VI)$$

wherein R' has the meaning defined above to form a compound having the general formula VII

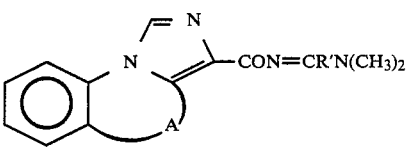  (VII)

wherein R' and —A— have the meanings set forth above and reacting the compound having the formula (VII) with $NH_2OH$ or another aminating agent to form a compound having the formula I wherein —A— has the meaning set forth above and
wherein X is

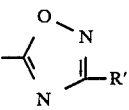

wherein R' has the meaning defined above, (d) reacting a compound having the general formula VIII

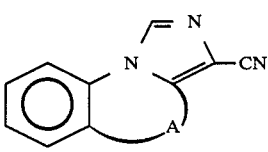  (VIII)

wherein —A— has the meaning set forth above, with NH₂OH to form a compound having the general formula IX

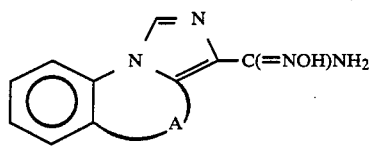
(IX)

wherein —A— has the meaning set forth above and reacting the compound thus obtained with R'—COCl, to form a compound of formula I, wherein X is

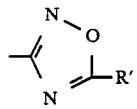

wherein R' has the meaning defined above.

Z is a leaving group, such as the —OP(O)(O-ethyl)₂) group hereof. Alternatively, the leaving group may be any disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)₂ wherein R is lower-alkyl, or —OP(O)(NR'R")₂ wherein R' and R" each represents lower-alkyl, or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (—40) degrees Celsius to about room temperature is accordingly usually particularly suitable.

The starting materials may be prepared by well known methods and from commercially available compounds.

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 1–100 mg in a pharmaceutically acceptable carrier per unit dosage.

The dosage of the compounds according to this invention is 1–100 mg/day, preferably 1–30 mg/day, when administered to patients, e.g. humans, as a drug.

A typical tablet which may be prepared by conventional tabletting techniques contains:

| | |
|---|---|
| Active compound | 1.0 mg |
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

Due to their high degree of affinity for the TBPS binding site, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the socalled TBPS binding site, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their TBPS binding site affinity. Suitable dosage ranges are 1–100 milligrams daily 1–30 milligrams daily, and especially 1–10 milligrams daily, depending as usual upon the exact mode of administration, form in which administered, the indication toward which the administration is directed, the subject involved and the body weight of the subject involved, and the preference and experience of the physician or veterinarian in charge. Broader ranges for dosages of the compounds according to this invention are 0.1–100 mg/day, preferably 1–30 mg/day, when administered to ptients, e.g., humans, as a drug.

The invention will now be described in further detail with reference to the following examples:

EXAMPLE 1

A. 1,2,3,4-tetrahydro-2-oxo-4,1-benzothiazepine a. methyl (o-nitrobenzylthio)-acetate A mixture of o-nitrobenzylchloride (17.2 g), methyl mercaptoacetate (8.9 ml), and potassium carbonate (27.6 g) was refluxed with stirring in acetone (200 ml) for 6 hours. The reaction mixture was filtered and evaporated to leave the title compound as an oil.

b. methyl (o-aminobenzylthio)-acetate

Methyl (o-nitrobenzylthio)-acetate (24.4 g) was dissolved in ethanol (500 ml). Raney nickel was added and the mixture was hydrogenated at room temperature and 1 atm. of hydrogen pressure. The title compound was obtained as an oil after filtration and evaporation of the reaction mixture.

c. 1,2,3,4-tetrahydro-2-oxo-1,4-benzothiazepine

Methyl (o-aminobenzylthio)-acetate was heated on a steambath in 40 ml 4N NaOH for 30 min. Thereby was formed a clear solution. After the solution had returned to room temperature it was neutralized (4N HCl) and extracted twice with ethyl acetate. The combined organic phases were dried over MgSO$_4$ and evaporated. The oily residue was then dissolved in polyphosphoric acid (100 g) and the solution was heated to 150° C. for 6 hours, whereafter it was poured into ice water (500 ml). The precipitated title compound was collected by filtration.

M.p. 213°–217° C.

B. 1,2,3,4-tetrahydro-2-oxo-4,1-benzoxazepine 20 g o-nitro benzylalcohol and 21.7 ml ethyl bromoacetate was dissolved in 250 ml dry DMF. Portions of 55–60% sodium hydride were added to this solution under stirring over one hour until a total amount of 8.5 g had been added. The mixture was left overnight at room temperature and then heated to 150° C. under stirring for 2 hours. The mixture was then evaporated and the residue was partitioned between diethylether and water. The organic phase was evaporated to give 14 g ethyl (o-nitro-benzyloxy) acetate as an oil.

14 g Ethyl(o-nitro-benzyloxy)acetate were dissolved in 300 ml 96% ethanol and 1.5 g 5% Pd on carbon was added. The mixture was then hydrogenated at normal pressure and room temperature. After completion of the reaction the mixture was filtered and the filtrate was added to 50 ml 4N NaOH and the resulting solution was left at room temperature for 2 hours, whereafter 50 ml 4N HCl were added. The mixture was evaporated, and the residue was stirred with 200 ml acetone. The mixture was filtered. The filtrate was evaporated to give o-amino-benzyloxy acetic acid as an oil.

1 g o-amino-benzyloxy acetic acid and 1.1 g dicyclohexyl carbodiimide were stirred in 15 ml refluxing methanol for 8 hours. The mixture was evaporated, and the residue was stirred with 50 ml acetone and filtered, whereafter the filtrate was evaporated to give the title compound.

M.p. 160°–165° C.

C. 2,3,4,5-Tetrahydro-4-methyl-2-oxo-1H-1,4-benzodiazepine

A mixture of 8.6 g o-nitrobenzyl chloride, 7.6 g sarcosine ethyl ester hydrochloride and 13.8 g K$_2$CO$_3$ was refluxed in 300 ml acetone for 16 hours, whereafter the mixture was filtered and evaporated. The oily residue was partitioned between ether/1N HCl. The aqueous phase was separated and pH was adjusted to 10 with dil. NaOH, whereafter it was extracted with dichloromethane. The organic phase was dried over Na$_2$SO$_4$ and evaporated. This left an oil which was hydrogenated using a standard procedure by means of 5% PD/C to give N-(o-aminobenzyl)sarcosine ethyl ester as an oil.

2.0 g N-(o-aminobenzyl)sarcosine ethyl ester was dissolved in 40 g polyphosphoric acid and the mixture was heated to 150° C. for two hours, then cooled and charged with 300 ml icewater.pH was adjusted to 8 with 50% NaOH and the mixture was extracted with dichloromethane. The organic phase was dried over Na$_2$SO$_4$ and evaporated to give the title compound.

M.p. 113°–114° C.

D. 3,4-Dihydro-3-oxo-2H-1,4-benzothiazine

A solution of bromo acetylbromide in toluene (20 ml) was added dropwise to an ice-cooled stirred solution of o-mercaptoaniline (10 mmol, 2.5 g) in a mixture of pyridine and toluene (50 ml, 30 ml). The mixture was allowed to heat to room temperature and stirring continued for 2 hours followed by reflux for 30 min., whereafter water (100 ml) was added. The organic phase was separated, dried (MgSO$_4$) and evaporated to give 3,4-dihydro-3-oxo-2H-1,4-benzothiazine.

M.p. 170°–171° C.

The following compound was synthesized from the appropriate aniline in an analogous manner:

3,4-dihydro-3-oxo-2H-1,4-benzoxazine.

M.p. 150.5° C.

E. 2,3,4,5-Tetrahydro-2-oxo-1H-1-benzazepine

A mixture of 4.0 g 1-tetralone oxime and 50 g polyphosphoric acid was stirred for 3 hours at 120° C. The mixture was then cooled and charged with 200 ml icewater. Filtration gave the title compound.

M.p. 135°–136° C.

F. 3-cyclopropyl-5-isocyanomethyl-1,2,4-oxadiazole a. 3-cyclopropyl-5-formylaminomethyl-1,2,4-oxadiazole

A solution of ethyl formylaminomethyl-carboxylate (150 mmol) and and cyclopropylcarboxamidoxime (100 mmol) in 100% EtOH (100 ml) was charged with Na (200 mg) and crushed molecular sieves (4 Å) (10 g). The stirred reaction mixture was heated to reflux for 8 h. The mixture was cooled to room temperature, filtered through filter aid and the filtrate was evaporated in vacuo. The oily residue was partitioned into a $CHCl_3$ phase, dried with $Na_2SO_4$, and evaporated.

b. 3-cyclopropyl-5-isocyanomethyl-1,2,4-oxadiazole

A stirred solution of 3-cyclopropyl-5-formylaminomethyl-1,2,4-oxadiazole (60 mmol) and triethylamine (176 mmol) in $CH_2Cl_2$ (100 ml) was charged at 0° C. dropwise with $POCl_3$ (60 mmol). The mixture was then left for 30 min. with stirring at 0° C., whereafter a solution of $Na_2CO_3$ (60 mmol) in $H_2O$ (50 ml) was added. The mixture was heated to room temperature, whereafter the organic phase was separated, dried and evaporated in vacuo. The residue was treated with ether, decanted, and the solution was evaporated to give the title compound as an oil. The oil was processed without any further purification. The compound was characterized by its IR absorption at 2160 $cm^{-1}$.

3-ethyl-5-isocyanomethyl-1,2,4-oxadiazole was prepared from 3-ethyl-5-formylaminomethyl-1,2,4-oxadiazole in a similar manner.

IR: 2170 $cm^{-1}$.

G. 5-Cyclopropyl-3-isocyanomethyl-1,2,4-oxadiazole a. Formylaminomethyl-carboxamideoxime

To 53.6 g (0.638 mol) N-formylamino-acetonitrile was added 0.55 mol freshly liberated hydroxylamine dissolved in 370 ml methanol. An ice bath was used to keep the temperature below 20° C. during addition. The solution was allowed to stand at room temperature overnight, whereafter it was evaporated to give the title compound as pale crystals. Decomp. 104°–110° C.

b. 3-Formylaminomethyl-5-ethyl-1,2,4-oxadiazole

A mixture of 70 ml ethyl propionate, 20 g formylaminomethylcarboxamideoxime, 1 g sodium and 30 g crushed mol. sieves (4 Å) was refluxed in 300 ml abs EtOH for 5 hours. The reaction mixture was filtered and the filtrate was evaporated. The oily residue was suspended in 300 ml $CHCl_3$, filtered and the filtrate was evaporated to give the title compound as an oil.

H-NMR (60 HMZ, $CDCl_3$) (ppm): 1.4(3H, t, J=8 Hz), 2.9(2 H, q, J=8 Hz), 4.55 (2 H, s), 7.8 (1 H, broad-NH), 8.25 (1 H, s).

The following compounds were synthesized from the appropriate ethyl esters:

3-Formylaminomethyl-5-cyclopropyl-1,2,4-oxadiazole
H-NMR (60 MHz, $CCDl_3$) (ppm): 1.2 (4 H, m), 2.8 (1 H, m), 4.5 (2 H, d, J=6 Hz), 7.8 (1 H, broad-NH), 8.2 (1 H, s).

3-Formylaminomethyl-5-methyl-1,2,4-oxadiazole
H-NMR (60 MHz, $CDCl_3$) (ppm): 2.6 (3 H, s), 4.6 (2 H, d, J=3 Hz), 7.4 (1 H, broad-NH), 8.25 (1 H, s).

3-Formylaminomethyl-5-methoxymethyl-1,2,4-oxadiazole H-NMR (60 MHz, $CDCl_3$) (ppm): 3.5 (3 H, s), 4.7 (4 H, s+d, J=6 Hz), 7.8 (1 H, broad=NH), 8.25 (1 H, s).

c. 5-Cyclopropyl-3-isocyanomethyl-1,2,4-oxadiazole

A stirred solution of 5-cyclopropyl-3-formylaminomethyl-1,2,4-oxadiazole (60 mmol) and triethylamine (176 mmol) in $CH_2Cl_2$ (100 ml) was charged dropwise with $POCl_3$ (60 mmol) at 0° C. The mixture was then left for 30 min. with stirring at 0° C., whereafter a solution of $Na_2CO_3$ (60 mmol) in $H_2O$ (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR stretching band at 2160 $cm^{-1}$.

5-Ethyl-3-isocyanomethyl-1,2,4-oxadiazole, 5-methyl-3-isocyanomethyl-1,2,4-oxadiazole, and 5-methoxymethyl-3-isocyanomethyl-1,2,4-oxadiazole were prepared in a similar manner. All compounds were oils and were characterized by their IR stretching band at 2160 $cm^{-1}$.

H. 3-(5-ethyl-1,2,4-oxadiazol-3-yl)-5,6-dihydro-4H-imidazo (1,5-a)(1)benzazepine 2,3,4,5-tetrahydro-2-oxo-1H-1-benazazepine (10 mmol) was dissolved in dry DMF (15 ml) and charged with sodium hydride (13 mmol. The resulting solution was cooled under $N_2$ to −20° C., whereafter chlorodiethylphosphate (13 mmol) was added. The reaction mixture was kept under $N_2$ with stirring at −20° C. and was charged with a −30° C. cold solution of 5-ethyl-3-isocyano-methyl-1,2,4-oxadiazol (13 mmol) and K-t-butylate (13 mmol) in dry DMF (10 ml). The resulting reaction mixture was allowed to heat to room temperature, whereafter 5 ml of glacial acetic acid was added. The resulting mixture was filtered which gave 0.36 g of the title compound.

M.p. 150.7°–150.8° C.

The following compounds were synthesized in an analogous manner.

Ethyl 4H-imidazo(5,1-c)(1,4)benzothiazine-3-carboxylate. M.p. 135.0° C. by reaction between ethyl isocyanoacetate and 3,4-dihydro-3-oxo-2H-1,4-benzothiazine.

Ethyl 4H-imidazo(5,1-c)(1,4)benzoxazine-3-carboxylate, M.p. 138.0° C. by reaction between ethyl isocyanoacetate and 3,4-dihydro-3-oxo-2H-1,4-benzoxazine.

Ethyl 5,6-dihydro-4H-imidazo(1,5-a)(1)benzazepine-3-carboxylate, M.p. 157.4°–159.6° C. by reaction between ethyl isocyanoacetate and 2,3,4,5-tetrahydro-2-oxo-1H-1-benazazepine.

Ethyl 5,6-dihydro-5-methyl-4H-imidazo(1,5-a)(1,4)benzodiazepine-3-carboxylate, M.p. 114.3°–116.7° C. by reaction between ethyl isocyanoacetate and 2,3,4,5-tetrahydro-4-methyl-2-oxo-1H-1,4-benzodiazepine.

Ethyl 4H,6H-imidazo(5,1-c)(4,1)-benzoxazepine-3-carboxylate, M.p. 142.0°–142.6° C. by reaction between ethyl isocyanoacetate and 1,2,3,4-tetrahydro-2-oxo-4,1-benzoxazepine.

Ethyl 4H,6H-imidazo(5,1-c)(4,1)benzthiazepine-3-carboxylate, M.p. 171.4°–171.7° C. by reaction between ethyl isocyanoacetate and 1,2,3,4 tetrahydro-2-oxo-4,1-benzthiazepine.

EXAMPLE 2

A. Methoxy acetamide oxime 2.3 g of sodium in 30 ml of dry methanol were mixed with 6.55 g of hydroxylamine hydrochloride in 66 ml of dry methanol. The mixture was filtered and 7.8 g of methoxyacetonitrile were added dropwise to the filtrate. The mixture was left for 48 hours at room temperature. The mixture was then cooled to 4° C. Filtration and evaporation gave the title compound.

The following compounds were synthesized from appropriate nitriles in an analogous manner:
propionamide oxime
cyclopropyl carboxamide oxime
iso-propyl carboxamide oxime
acetamide oxime
benzamide oxime

B. 3-(3-methoxymethyl-1,2,4-oxadiazol-5-yl)-5,6-dihydro-4H-imidazo(1,5-a(1)benzazepine 50 mg of sodium was dissolved in 20 ml of dry ethanol containing 3 g of molecular sieves (4 Å) and 9.5 g of methoxyacetamide oxime was added to this mixture and thereupon 0.5 g of ethyl 5,6-dihydro-4H-imidazo(1,5-a)(1)benzazepine-3-carboxylate was added. The resulting mixture was refluxed for 12 hours, whereafter it was cooled and the molecular sieves were filtered off. The title compound was isolated by evaporation of the solvent in vacuo followed by addition of icewater and filtration.

M.p. 115.6°–115.8° C.

The following compounds were prepared in exactly the same manner:

3-(3-cyclopropyl-1,2,4-oxadiazol-5-yl)-4H,6H-imidazo(5,1-c)(4,1)benzthiazepine, M.p. 165.5°–162.0° C. by reaction between cyclopropylcarboxamide oxime and ethyl 4H,6H-imidazo(5,1-c)(4,1)benzthiazepine-3-carboxylate.

3-(3-ethyl-1,2,4-oxadiazol-5-yl)-5,6-dihydro-4H-imidazo(1,5-a)(1)benzazepine, M.p. 166.1° C. by reaction between propionamide oxime and ethyl 5,6-dihydro-4H-imidazo(1,5-a)(1)benzazepine-3-carboxylate.

3-(3-ethyl-1,2,4-oxadiazol-5-yl)-4H-imidazo(5,1-c)(1,4)benzoxazine, M.p. 133.7° C. by reaction between propionamide oxime and ethyl 4H-imidazo(5,1-c)(1,4)benzoxazine-3-carboxylate.

3-(3-ethyl-1,2,4-oxadiazol-5-yl)-4H-imidazo(5,1-c)(1,4)benzothiazine, M.p. 144.0° C. by reaction between propionamide oxime and ethyl 4H-imidazo(5,1-c)(1,4)benzothiazine-3-carboxylate.

3-(3-phenyl-1,2,4-oxadiazol-5-yl)-5,6-dihydro-4H-imidazo(1,5-a)(benzazepine, M.p. 169°–171° C. by reaction between benzamide oxime and ethyl 5,6-dihydro-4H-imidazo(1,5-a)(1)benzazepine-3-carboxylate.

3-(3-methyl-1,2,4-oxadiazol-5-yl)-5,6-dihydro-4H-imidazo(1,5-a)(1)benzazepine, M.p. 173.5°–174.2° C. by reaction between acetamide oxime and ethyl 5,6-dihydro-4H-imidazo(1,5-a)(1)benzazepine-3-carboxylate.

3-(3-cyclopropyl-1,2,4-oxadiazol-5-yl)-5,6-dihydro-4H-imidazo(1,5-a)(benzazepine, M.p. 147.2°–147.3° C. by reaction between cyclopropyl carboxamide oxime and ethyl 5,6-dihydro 4H-imidazo(1,5-a(1)benzazepine-3-carboxylate.

In conclusion, from the foregoing, it is apparent that the present invention provides novel neurologically-effective TBPS-binding compounds and salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. Heterocyclic compounds having the formula I

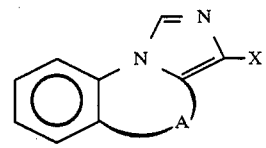

wherein
X is

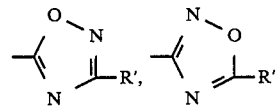

or $CO_2R'$
wherein
R' is $C_{1-6}$-alkyl, $C_{3-7}$-cycloalkyl, or $C_{1-3}$-alkoxymethyl, and
A— is —$(CH_2)_n$—Y—$(CH_2)_m$—,
wherein n and m are 1 and —Y— is —$CH_2$—.

2. A compound of claim 1 which is is 3-(3-ethyl-1,2,4-oxadiazol-5-yl)-5,6-dihydro-4H-imidazo (1,5-a)(1)benzazepine.

3. A compound of claim 1 which is 3-(5-ethyl-1,2,4-oxadiazol-3-yl)-5,6-dihydro-4H-imidazo (1,5-a)(1)benzazepine.

4. A pharmaceutical composition suitable for use as an anti-convulsant, anxiolytic, hypnotic, sedative, nootropic, anthelmintic, ecto- and endoparasitic, insecticide, and acaricide in human and animal health, comprising an amount of a compound of claim 1 which is effective for such purpose, together with a pharmaceutically-acceptable carrier or diluent.

5. A pharmaceutical composition according to claim 4 wherein it is in the form of an oral dosage unit containing 1-100 mg of the active compound.

6. A method of treating a subject having a condition requiring anticonvulsant, anxiolytic, hypnotic, sedative, nootropic, anthelmintic, ecto- or endoparasitic, insecticidal, or acaricidal treatment, comprising the step of administering to said subject an amount of a compound of claim 1 which is effective for the alleviation of such condition.

7. A method of treating a subject having a condition requiring anticonvulsant, anxiolytic, hypnotic, sedative, nootropic, anthelmintic, ecto- or endoparasitic, insecticidal, or acaricidal treatment, comprising the step of administering to said subject an amount of a compound of claim 1 which is effective for the alleviation of such condition in the form of a pharmaceutical composition thereof, in which it is present together with a pharmaceutically-acceptable carrier or diluent.

* * * * *

UNITED STATES PATENT AND TRADEMARK OFFICE
CERTIFICATE OF CORRECTION

PATENT NO. : 4,870,073
DATED : September 26, 1989
INVENTOR(S) : Frank Watjen, Mogens Engelstoft It is certified that error appears in the above-identified patent and that said Letters Patent is hereby corrected as shown below:

Col. 1, line 13; insert -- , -- after "endoparasiticides"

Col. 1, line 25; "dound" should read -- found --

Col. 1, line 27; "radiac-" should read -- radioac- --

Col. 1, line 30; "macetical" should read -- maceutical --

Col. 1, line 56; "werein" should read -- wherein --

Col. 5, line 23; delete last ")" in line

Col. 7, line 25; "ptients," should read -- patients, --

Col. 9, line 59; "CCDl$_3$)" should read -- CDCl$_3$) --

Col. 10, line 29; insert -- ) -- after "mmol"

Col. 11, line 22; "9.5" should read -- 0.5 --

Col. 11, line 63; insert -- ) -- after "(1,5-a"

Signed and Sealed this

Twenty-third Day of October, 1990

*Attest:*

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,870,073
DATED : September 26, 1989
INVENTOR(S) : Frank Wätjen and Mogens Engelstoft It is certified that error appears in the above-identified patent and that said Letters Patent is hereby corrected as shown below:

Col. 2, line 26; "25 1" should read -- 25 µl --

Col. 3, line 35; "above mentioned" should read above-mentioned --

Col. 6, line 2; "to hundred" should read -- to one hundred --

Col. 8, line 41; "icewater.pH" should read -- icewater. The pH --

Col. 6, line 66; "socalled" should read -- so-called --

Col. 9, line 7; delete "and" (second occurrence)

Col. 6, lines 38 & 39; "pharmaceutically acceptable" should read -- pharmaceutically-acceptable --

Signed and Sealed this

Twelfth Day of November, 1991

Attest:

HARRY F. MANBECK, JR.

*Attesting Officer*     *Commissioner of Patents and Trademarks*